US009585622B2

(12) United States Patent
Sattler et al.

(10) Patent No.: US 9,585,622 B2
(45) Date of Patent: Mar. 7, 2017

(54) APPARATUS AND METHOD FOR DATA PROCESSING OF PHYSIOLOGICAL SIGNALS

(75) Inventors: Frank Sattler, Lübeck (DE); Marcus Eger, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 553 days.

(21) Appl. No.: 14/111,222

(22) PCT Filed: Apr. 5, 2012

(86) PCT No.: PCT/EP2012/001523
§ 371 (c)(1),
(2), (4) Date: Dec. 17, 2013

(87) PCT Pub. No.: WO2012/139737
PCT Pub. Date: Oct. 18, 2012

(65) Prior Publication Data
US 2014/0142395 A1     May 22, 2014

(30) Foreign Application Priority Data
Apr. 12, 2011   (DE) .................. 10 2011 016 804

(51) Int. Cl.
*A61B 5/04* (2006.01)
*A61B 5/00* (2006.01)
(Continued)

(52) U.S. Cl.
CPC .............. *A61B 5/725* (2013.01); *A61B 5/021* (2013.01); *A61B 5/0205* (2013.01);
(Continued)

(58) Field of Classification Search
CPC ............ A61B 5/0488; A61M 16/0051; A61M 2210/1014
(Continued)

(56) References Cited

U.S. PATENT DOCUMENTS

| 4,248,240 A | 2/1981 | Van Eykern |
| 4,915,103 A | 4/1990 | Visveshwara et al. |

(Continued)

FOREIGN PATENT DOCUMENTS

| AU | 707148 B2 | 7/1997 |
| DE | 42 35318 A1 | 9/1993 |

(Continued)

*Primary Examiner* — Carl H Layno
*Assistant Examiner* — Jon Eric C Morales
(74) *Attorney, Agent, or Firm* — McGlew and Tuttle, P.C.

(57) ABSTRACT

A filter apparatus (100) having a signal input (101) to which an input signal is applied which contains a useful component and a noise component, a fast signal path (102) and a slow signal path (103) arranged in parallel therewith. The fast signal path and the slow signal path are coupled to the signal input. The fast signal path contains a filter in order to prompt fast filtering of the input signal. The slow signal path contains a filter in order to prompt slow filtering of the input signal. An output of the slow signal path is coupled to the fast signal path by means of a signal line (106). A signal output (104) which is coupled to the fast signal path has an output signal applied to it which essentially contains useful components of the input signal.

10 Claims, 7 Drawing Sheets

(51) Int. Cl.
*H03H 17/02* (2006.01)
*A61B 5/0402* (2006.01)
*A61B 5/0205* (2006.01)
*A61B 5/021* (2006.01)
*A61B 5/0488* (2006.01)
*A61B 5/145* (2006.01)
*A61M 16/00* (2006.01)
*H03H 21/00* (2006.01)

(52) U.S. Cl.
CPC ........ *A61B 5/0402* (2013.01); *A61B 5/04012* (2013.01); *A61B 5/0488* (2013.01); *A61B 5/14542* (2013.01); *A61B 5/4836* (2013.01); *A61B 5/7203* (2013.01); *A61M 16/0051* (2013.01); *A61M 16/0057* (2013.01); *H03H 17/0261* (2013.01); *H03H 17/0294* (2013.01); *A61M 16/00* (2013.01); *A61M 2230/00* (2013.01); *A61M 2230/005* (2013.01); *A61M 2230/04* (2013.01); *A61M 2230/42* (2013.01); *A61M 2230/60* (2013.01); *H03H 2021/0083* (2013.01)

(58) Field of Classification Search
USPC ..................................... 600/546; 128/204.23
See application file for complete search history.

(56) References Cited

U.S. PATENT DOCUMENTS

| | | | |
|---|---|---|---|
| 5,259,387 A | 11/1993 | DePinto | |
| 5,318,036 A | 6/1994 | Arand et al. | |
| 5,353,788 A | 10/1994 | Miles | |
| 5,777,909 A | 7/1998 | Leung et al. | |
| 5,820,560 A | 10/1998 | Sinderby et al. | |
| 5,980,463 A | 11/1999 | Brockway et al. | |
| 6,411,843 B1* | 6/2002 | Zarychta | 600/546 |
| 6,588,423 B1 | 7/2003 | Sinderby | |
| 7,535,859 B2 | 5/2009 | Brox | |
| 2004/0260186 A1 | 12/2004 | Dekker | |
| 2006/0056641 A1 | 3/2006 | Nadjar et al. | |
| 2006/0152197 A1 | 7/2006 | Stanesti et al. | |
| 2008/0288199 A1 | 11/2008 | Batruni | |
| 2008/0308104 A1 | 12/2008 | Blomberg et al. | |
| 2009/0122930 A1 | 5/2009 | Menkhoff | |
| 2009/0143693 A1 | 6/2009 | Ye et al. | |
| 2010/0168595 A1 | 7/2010 | Lee et al. | |

FOREIGN PATENT DOCUMENTS

| | | |
|---|---|---|
| DE | 195 18 528 A1 | 1/1996 |
| DE | 42 35318 C2 | 2/1997 |
| DE | 199 59 822 A1 | 6/2001 |
| DE | 101 64 446 A1 | 7/2003 |
| DE | 10 2007 024 072 A1 | 11/2007 |
| DE | 10 2007 062 214 B3 | 8/2009 |
| DE | 197 28 782 B4 | 12/2009 |
| EP | 0 677 922 A2 | 10/1995 |
| EP | 0 749 056 B1 | 12/1996 |
| EP | 0 889 291 A2 | 1/1999 |
| EP | 1 346 743 A1 | 9/2003 |
| EP | 1 365 296 A1 | 11/2003 |
| EP | 1 793 374 A1 | 6/2007 |
| WO | 98/48877 A1 | 11/1998 |
| WO | 2006/039529 A2 | 3/2006 |
| WO | 2006/131149 A1 | 12/2006 |
| WO | 2009/096820 A1 | 8/2009 |

* cited by examiner

Unfiltered input signal Fig. 5A

Signal component above fixed Fig. 5B

Signal component above adapted Fig. 5C

Fig. 6

APPARATUS AND METHOD FOR DATA PROCESSING OF PHYSIOLOGICAL SIGNALS

CROSS REFERENCE TO RELATED APPLICATIONS

This application is a United States National Phase Application of International Application PCT/EP2012/001523 filed Apr. 5, 2012 and claims the benefit of priority under 35 U.S.C. §119 of German Patent Application DE 10 2011 016 804.4 filed Apr. 12, 2011, the entire contents of which are incorporated herein by reference.

FIELD OF THE INVENTION

The present invention pertains, in general, to the area of the processing of physiological signals and especially to an apparatus and to a method for processing physiological signals, especially physiological signals of human beings, for therapeutic and diagnostic applications as well as monitoring applications ("monitoring"). A special case is the use of such signal or data processing with the use of a filter apparatus in the control of the respiration of a patient by a respirator.

BACKGROUND OF THE INVENTION

Signals of sensors, which are used to detect physiological properties, cannot typically be used further directly, but must be filtered in a suitable manner. This serves especially the purpose of separating the desired useful signal, for example, an ECG signal, from undesired signals, e.g., noise or motion artifacts, in order to let thereby the useful signal proper stand out more clearly.

Various methods have long been known for carrying out such a filtering. These methods are based mostly on so-called linear filters, which can be described by linear mathematical transformations (e.g., Fourier transformation). Linear filters can be designed as comparatively simple filters and possess signal-independent properties, i.e., the properties do not depend on the signal being processed. Such filters are typically characterized by a so-called system function, which reflects the frequency response and the phase response.

However, any form of signal processing ("filtering") is associated, in principle, with a certain time requirement. This means that the processed signal is available at the output of the signal-processing unit after a certain delay time only. The value of the delay time depends, on the other hand, very decisively on the filter properties.

However, this delay time must not exceed a certain limit in case of some applications, especially during the processing of physiological signals, because, e.g., a medical engineering device must change its characteristic fast enough to serve its purpose. For example, a respirator must be able to respond fast enough to the wish of a patient to be respirated, because respiration cannot otherwise be carried out adequately.

Since there are physiological signals, which require, on the one hand, a large amount of filtering, i.e., a high filter quality, but only short delay times are permissible, on the other hand, an especially high requirement on signal processing, i.e., on the filter being used, will arise here.

Linear filters reach their limits in a short time here, because, in particular, their ability to separate signals ("filter slope" or "bandwidth") is linked directly with the delay time. Strictly speaking, there is a relationship between the settling time and the frequency bandwidth needed therefor. One speaks of time-bandwidth product here in the theory of filters. This means that the product of the settling time by the frequency bandwidth is constant. This relationship is fundamental and is inherently due to the linear properties of these filters. Therefore, there is no possibility to build narrow-band filters or filters having a steep cut-off with a very short delay time. Long settling times mean that the filter generates artifacts, which are of a long duration. In other words, any brief change in the input signal generates at the output a filter artifact of a long duration. This phenomenon is known under the term "transient response." In other words, stated more simply, linear filters possess either poor properties in case of short delay times or good properties in case of long delay times.

Besides the classic linear filters, there are filters which, contrary to linear filters, can partly process time-variant signals and are partly based on nonlinear methods. Examples herefor are Blind Source Separation, Independent Component Analysis, Principal Component Analysis, Adaptive Filters and Empirical Mode Decomposition. Even though some of these filters possess considerably better properties than classic linear filters, the effort needed for signal processing that is associated with them is great, and longer or shorter delay times will always arise. Therefore, these filters cannot be used for all applications.

Therefore, only another type of nonlinear filters can be considered for these applications. In particular, the settling time or the duration of filter artifacts and the filter quality ("filter slope" or "bandwidth") cannot be uncoupled from each other in nonlinear filters. One example of such a filter is a threshold value detector, which sets all values above a certain threshold, e.g., to zero. The time delay is obviously very short here, because a threshold value comparison can be performed very fast and, furthermore, no filter artifacts will appear. Consequently, there is no post-pulse oscillation in these filters.

Various filter solutions are known from the state of the art.

Thus, DE 42 35 318 C2 describes an apparatus for removing a baseline fluctuation from an ECG signal, in which a forward filter and a backward filter are connected in series via a buffer. An ECG signal is applied here to the forward filter, which has a nonlinear phase response characteristic and generates filtered signal data. These data are stored in the buffer, and blocks of the stored data are applied in reversed chronological order to the likewise nonlinear backward filter in order to generate blocks filtered in the backward direction in this manner.

DE 197 28 782 B4 pertains to a nonlinear filter for transducer signals having a vibration component for use in motor vehicles. The transducer signals are applied to an input of the filter, and a difference of an output signal of the filter from this input signal is formed in a differentiating member, and the difference thus formed is sent to an integrating member once directly and once via a nonlinear transmission member. The nonlinear transmission member is provided with a middle zone of relatively low gain, which has a variable width, with the width of the middle zone being adjusted by an amplitude detector, which forms the amplitude difference between the highest signal value and the lowest signal value of the filter input signal during each vibration period duration of the interfering vibration in the input signal, such that the time constant of the filter is reduced to a low value only during changes in the useful signal and the unwanted signal does not therefore appear at the filter output.

DE 195 18 528 A1 discloses a digital high-pass filter with means for restoring the baselines, wherein the high-pass filter is derived from a low-pass filter. The low-pass filter is formed by a first low-pass filter and a second low-pass filter, each of which receives a common input signal and outputs a corresponding output signal. The first filter has a relatively high limit frequency, so that it accurately follows the input signal, but does not significantly attenuate the ripple thereof. The second filter has a limit frequency that can be changed as a function of a control signal, which is generated on the basis of a comparison of the output signals of both filters.

EP 0 677 922 A2 pertains generally to a fast low-pass filter and a slow low-pass filter, wherein both filters receive the same input signal and the outputs of the two filters are compared in order to increase the response time of the slow low-pass filter if the difference of the outputs exceeds a certain value, so that the slow low-pass filter can follow the input signal faster.

EP 0 749 056 B1 shows a regenerative tracking filter using a plurality of integrators.

EP 1 346 743 A1 discloses a device for controlling a respirator with a breathing gas release control, which is connected to a sensor for a measured signal and builds up pressure as a function of a trigger signal corresponding to the measured signal.

EP 1 793 374 A1 pertains to a filter apparatus for active noise reduction.

U.S. Pat. No. 4,248,240 shows an apparatus for detecting the activity of the respiratory organs and of the heart of a living being, in which EMG signals are filtered by means of a high-pass filter, with which a comparator is connected in parallel.

U.S. Pat. No. 5,777,909 pertains to a low-pass filter with coefficient switchover for improving the settling time.

U.S. Pat. No. 7,535,859 B2 pertains to the problem of speech activity recognition with the use of adaptive tracking of the background noise.

US 2009/0143693 A1 generally describes an apparatus for generating determination indices in order to identify ECG unwanted signals.

US 2010/0168595 A1 pertains to a method and an apparatus for eliminating a baseline shift with a first amplifier and a second amplifier, between which a low-pass filter is inserted. The output of the first amplifier is sent to the low-pass filter as well as to a time delay circuit connected in parallel to the low-pass filter, whose output signal is added to the output signal of the low-pass filter and is sent to the second amplifier.

The following documents shall be mentioned as further prior art: AU 707148 B2; DE 101 64 446 A1; DE 10 2007 024 072 A1; DE 10 2007 062 214 B3; EP 0 889 291 A2; EP 1 365 296 A1; U.S. Pat. No. 4,915,103; U.S. Pat. No. 5,353,788; U.S. Pat. No. 5,980,463; U.S. Pat. No. 6,588,423; US 2004/0260186 A1; US 2006/0152197 A1; WO 98/48877; WO 2006/131149 A1; WO 2006/029529 A1; DE 199 59 822 A1; U.S. Pat. No. 5,820,560 and WO 2009/096820 A1.

SUMMARY OF THE INVENTION

The object of the present invention is, in general, to overcome the drawbacks of the state of the art and especially to embody a fast real-time filtering while achieving at the same time a high filter quality, especially in the area of medical devices, for example, respirators.

The term real-time filtering is defined in the sense of the present invention such that filtering of the signal is applied to actually detected measured values and the results are available without essential time delay, i.e., without or with a slight delay or with a negligibly short delay.

A short delay is defined in the sense of the present invention as a delay of a signal that does not lead to no effects and loss of information concerning an undistorted reproduction or further processing of the signal in the case of a scanning and design of the analog circuit components adapted to the signal bandwidth by analog signal processing and amplification, analog-to-digital conversion, mathematical conversions and standardizations and digital-to-analog conversion. An approximate indicator for a scanning adapted to the signal bandwidth shall be based on the Nyquist criterion.

The exemplary embodiments selected in the present invention describe the filtering on the basis of at least two parallel signal paths, to which a common input signal is applied simultaneously in time. However, the term "parallel signal paths" is not limited to an absolutely necessary parallelism in the sense of multiprocessing, but it rather describes a "functional" parallelism. For example, a processing of signals, as it were, in a simultaneous manner, e.g., in a multiplexing or multitasking process, is defined as "functional" parallelism in the sense of the present invention, wherein the processing may also be carried out by means of one arithmetic-logic computing unit (ALU), one µC, µP or a similar type of processor. Each of the at least two signal paths is passed through by the input signal and filtered in the process specifically in each of these at least two signal paths. The output signals of these at least two signal paths are linked with one another in such a way that at least one of the at least two signal paths affects the other of the at least two signal paths and thus affects the output signal thereof, so that an improvement of signal filtering is achieved at the output of at least one signal path due to the effect of the at least one other signal path.

Signal filtering and real-time filtering comprise, in the sense of the present invention, many different types of filtering, which have as a result the same effect in the sense of the present invention. Thus, both filtering based on electronic components, for example, based on operational amplifier circuits with further components, such as diodes, resistors, capacitors or coils, also in suitable combination with peak value detectors, rectifiers, shift registers and other logic circuits are included in the sense of the present invention. An exemplary operational amplifier is known to the person skilled in the art as a Sallen-Key circuit. Furthermore, filter circuits based on programmable components are also included in the sense of the present invention. FPGA (Field Programmable Gate Array), PAL (Programmable Array Logic), GAL (Generic Array Logic), ASIC (Application-specific Integrated Circuit), CPLD (Complex Programmable Logic Device) or further analog programmable components, digital programmable components, as well as combinations of the types mentioned in the list may be mentioned as examples here as an incomplete list of programmable types of components.

Furthermore, also included as possibilities of signal filtering and real-time filtering in the sense of the present invention are various types of digital filtering, which are carried out after an analog-to-digital conversion in the form of a software-implemented filtering by a process control in the form of a programmable source code, in which filter coefficients and/or mathematical equation models are contained, which are carried out by means of a µP (microprocessor), µC (microcontroller) or a DSP (Digital Signal Processor) in various embodiments of filter types. Such filter types based on programmable source codes include, for example, FIR filters (Finite Impulse Response), IIR filters (Infinite Impulse Response), but also smoothing filters, Kalman filters, nonlinear filters as well as limiting filters or ranking filters.

Signal filtering and real-time filtering in the sense of the present invention are applied, for example, when driving a respirator on the basis of correspondingly filtered physiological signals of a patient. Such a respiration control requires a minimal delay time during the filtering of the physiological signal, so that the respiration control can respond to changing respiration needs without essential time delay.

The method according to the present invention for the real-time filtering of physiological signals, which is described below, makes it possible to separate the useful component of a physiological signal from noise components.

The method of real-time filtering of physiological signals with a useful component and with a noise component comprises a fast signal path and a parallel, slow signal path, through which the physiological signal passes, with a connection between the signal outputs of the fast signal path and of the slow signal path and with another connection between the signal output of the fast signal path with the signal input of the slow signal path, wherein the physiological signal is coupled in parallel into the input of the fast signal path and into the input of the slow signal path, wherein the fast signal path is passed through fast and a fast, preferably nonlinear filtering is performed, and a filtered output signal, which contains essentially the useful component of the physiological signal and in which the noise component of the physiological signal is not suppressed completely by the fast filtering, is present at the signal output of the fast signal path, wherein the characteristic of the fast signal path is influenced via the connection, wherein the slow signal path is passed through slowly and a slow, preferably nonlinear filtering is performed, wherein the characteristic of the slow signal path is influenced via the further connection, and wherein a filtered output signal, which contains essentially the useful component of the physiological signal and in which the noise component of the physiological signal is essentially suppressed by the slow filtering, is present at the signal output of the slow signal path, wherein a filtered output signal, which contains essentially the useful component of the physiological signal and in which the noise component of the physiological signal is essentially suppressed, is present at the signal output without time delay relative to the signal output of the fast signal path.

The application is shown in a preferred first exemplary embodiment (FIGS. 1A, 1B, 1C and 1D) of the present invention in the driving of a respirator on the basis of a correspondingly filtered electromyographic signal (EMG) from a patient. A minimal delay time is required during the filtering of the electromyographic signal in this application, so that the respiration control can respond to changing respiration needs without essential time delay. In this exemplary embodiment, the goal of filtering according to the present invention is to remove the ECG artifacts caused by the heartbeat of the patient, especially the R waves, without major time delay, without compromising the useful signal.

A conventional linear filtering (e.g., high-pass filter) would either lead to an excessively long delay time or a considerable part of the signal energy would be lost, because the cut-off frequency of the high-pass filter would have to be set at a correspondingly high value in order to sufficiently remove the ECG artifacts.

The above problem is solved by the signal path being divided during filtering into a plurality of separate signal paths, namely, into a fast signal path and at least one slow signal path. The signal paths act on the same noise-affected input signal, which contains both a useful component and a noise component (e.g., ECG artifacts). The result of filtering in the slow signal path is available only after a longer delay time and is then used, for example, in the form of parameters during the filtering in the fast signal path. This coupling of the slow signal path with the fast signal path is preferably designed such as to be suitable for affecting the functional characteristic of the slow signal path.

A fast signal path is defined in the sense of the present invention such that a signal passes through the fast path from the input to the output faster by a factor of 5 to 20 than it does through the slow signal path. To differentiate between the terms "fast signal path" and "slow signal path," it shall be understood that the signal travel time is shorter in the fast path by a factor of at least 2 than in the slow path. In preferred embodiments of the present invention, this factor has, in general, values between 2 and 25 and preferably between 5 and 20. A travel time of 20 msec is an example of and typical of a fast signal path in the sense of the present invention, and a travel time of 200 msec is an example of and typical of a slow signal path. The fast signal path shall, in principle, respond fast to changes of the input signal and make at the same time available at its output the smoothest possible envelope curve, which will then be used to drive a device. A certain time (reaction time), which may vary depending on the desired extent of smoothing and on the filters used, is, of course, necessary for smoothing the envelope curve. The usual travel or reaction times for the fast path are therefore in a range of preferably between about 20 msec and about 200 msec. Contrary to this, the travel or reaction times in the slow path are in a range of preferably between 200 msec and about 10 sec.

To remove ECG artifacts from an EMG useful signal, the signal paths are adapted to the signal components of the ECG signal and of the EMG signal.

Scanning in the range of 250 values per second to 1,500 values per second is necessary and advantageous for the ECG signal, and scanning in the range of 250 values per second to 1,500 values per second is necessary and advantageous for the EMG signal.

The filtered EMG useful signal shall be available for further use after a travel time for filtering in the range within one breathing cycle of a patient, i.e., in a range of 0.05 sec to 0.25 sec, for example, for controlling a respirator. In general, any other external device may also be coupled with the signal output of the filter apparatus instead of the respirator. The external device may be coupled via a signal line with the slow path. The signal output may be coupled, in principle, with the slow signal path in a preferred embodiment.

The fast signal path is designed on this basis with a travel time of 0.02 sec. The slow signal path is designed on the basis of the time curve of the ECG artifact with a typical travel time in the range of 0.3 sec to 1 sec.

However, it is definitely realistic in practice to design the travel time for the slow signal path in a range of 1 sec to 10 sec for a marked improvement of the suppression of the ECG artifacts in the EMG signal.

The resulting output signal ideally contains only the useful component. In reality, the noise component is only reduced more greatly than the useful component. A filter with nonlinear properties is preferably used at least in the fast signal path. The known methods of linear filtering, including adaptive filters, may be used in the slow signal path, because the longer delay time plays no role.

Figure 2:
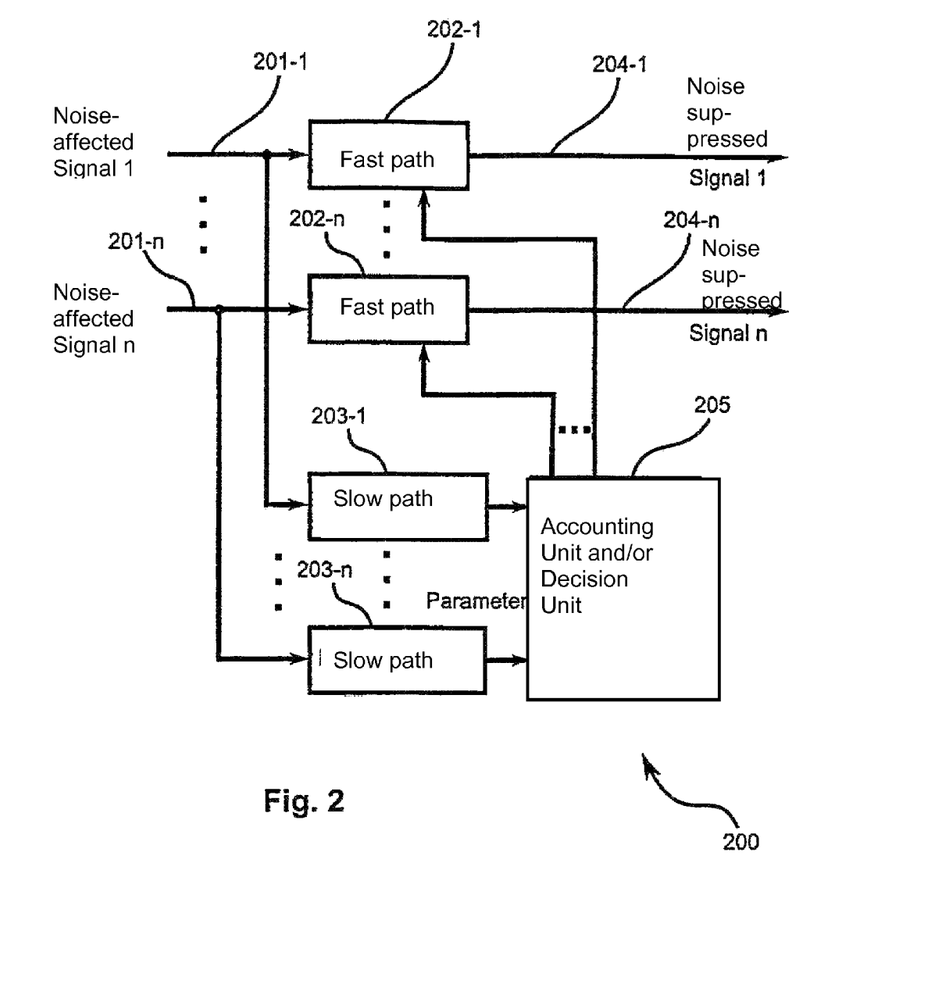
FIG. 2 is a schematic view of a second exemplary embodiment of the present invention, in which crosslinking of information between a plurality of signal paths is performed.

Information is cross linked between a plurality of signal paths in another, second exemplary embodiment (FIG. 2). Results of the slow filtering of a signal can thus be applied to the fast filtering of another signal. This second exemplary embodiment can be derived from the first exemplary embodiment by a replication and cross linking of the signal paths, and an additional accounting or decision unit (VE) is provided. As an alternative, the slow signal paths may be contained entirely in the decision unit.

In another, third exemplary embodiment (FIGS. 3A and 3B), there is additional feedback compared to the first exemplary embodiment from the output of the fast signal path or from an output of the fed external device to the slow signal path. Automatic adaptation of signal processing is made possible hereby.

In another, fourth exemplary embodiment (FIG. 4), there is additional feedback compared to the second exemplary embodiment from the outputs of the fast paths or from an output (or from a plurality of outputs) of the fed external device to the accounting/decision unit. As in FIGS. 3A and 3B, automatic adaptation of signal processing is made possible hereby.

The present invention will be described now on the basis of some exemplary embodiments with reference to the figures, which show different embodiments of the apparatus according to the present invention for the data processing of physiological signals and of the filter apparatus according to the present invention. Even though the following description pertains to an apparatus for data processing and to a filter apparatus for use in the control of a respirator, the apparatus according to the present invention may also be used, as is obvious to the person skilled in the art, for processing other physiological signals, for which it is important to remove noise signals without a major time delay without compromising the useful signal. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
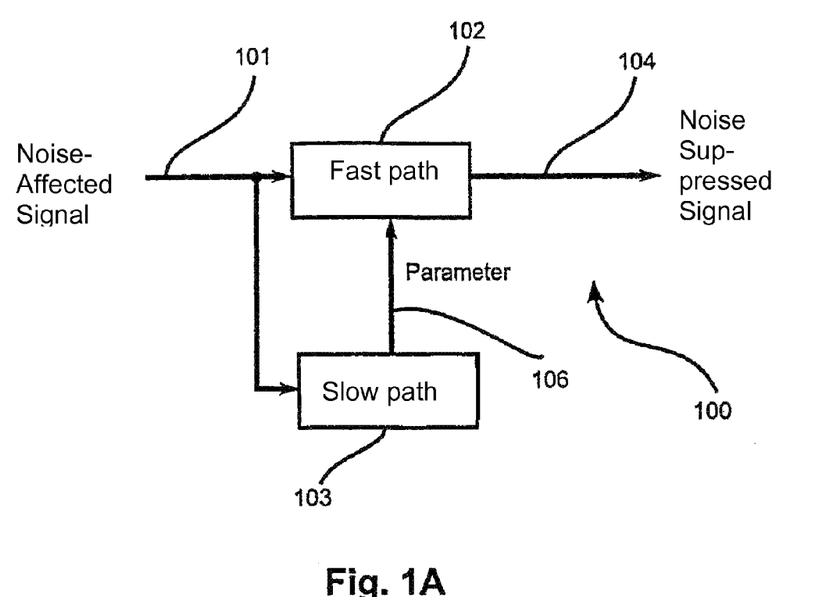
FIG. 1A is a schematic view of a first exemplary embodiment of the present invention, which can be used with the goal of real-time filtering for driving a respirator.

Referring to the drawings in particular, FIG. 1A shows a view of a first exemplary embodiment of a filter apparatus 100 according to the present invention. The filter apparatus 100 has a fast signal path 102 and at least one slow signal path 103, which are arranged in parallel. The signal paths 102 and 103 act on the same noise-affected input signal 101, which contains both a useful component and a noise component. The result of filtering in the slow signal path 103 is available after a rather long delay time only and is then used during the filtering in the fast signal path 102, for example, in the form of parameters. The slow signal path 103 is coupled for this with the fast signal path 102 via a signal line 106. The resulting output signal 104 ideally contains only the useful component. However, the noise component is in reality only reduced more greatly than the useful component. A filter possessing nonlinear properties is preferably used at least in the fast signal path 102. The known methods of linear filtering, including adaptive filter, may be used in the slow signal path 103, because the longer delay time plays no role.

The filter apparatus 100 from FIG. 1A is preferably used in the real-time filtering of physiological signals, for example, during the filtering of electromyographic signals from a patient, which are used to drive a respirator on the basis of the correspondingly filtered electromyographic signals. As was explained above, such respiration control requires a minimal delay time during the filtering of the electromyographic signal, which is achieved by means of the filter apparatus from FIG. 1A.

For example, filter apparatus 100 from FIG. 1A may be used with the aim of removing the ECG artifacts (e.g., the R waves) caused by the patient's heartbeat without major time delay, without compromising the useful signal in the process.

Figure 1B:
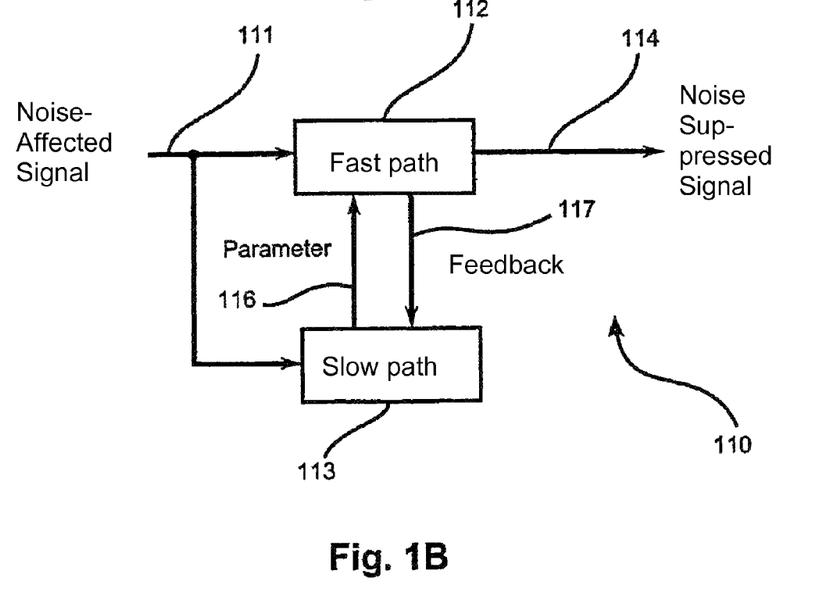
FIG. 1B is a variant of the exemplary embodiment from FIG. 1A.

FIG. 1B shows a variant of the filter apparatus shown in FIG. 1A. The filter apparatus 110 likewise has a fast signal path 112 and at least one slow signal path 113, which are arranged in parallel and act on the same noise-affected input signal 111. The result of filtering in the slow signal path 113 is available after a rather long delay time only and is then used during filtering in the fast signal path 112, for example, in the form of parameters. The slow signal path 113 is coupled for this with the fast signal path 112 via a signal line 116. Furthermore, a signal from the fast signal path 112, which does not have to be the output signal 114, is returned via a signal line 117 to the slow signal path 113 in order to affect the functional characteristic of the slow signal path 113 in this manner. For example, the speed of the slow signal path 113 can be adapted to the particular application within certain limits by means of this signal feedback.

Figure 1C:
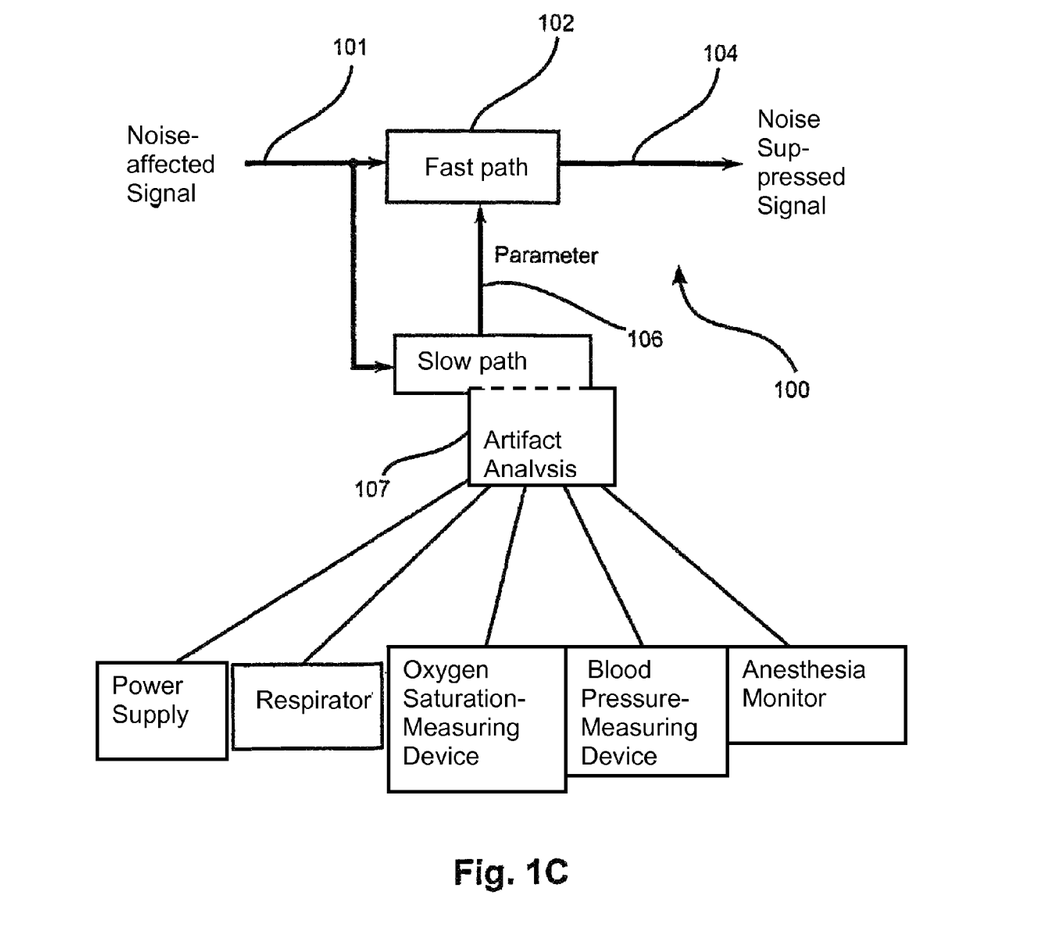
FIG. 1C is the embodiment from FIG. 1A, in which the "slow filter" is provided with an additional "artifact analysis" block, which has inputs for additional signals.

FIG. 1C shows an embodiment from FIG. 1A, in which the slow signal path 103 is provided with an additional "artifact analysis" block 107, which has inputs for additional signals. These additional signals originate, for example, from external sources (sources for unwanted signals) or external apparatuses, which generate unwanted signals in the form of voltages and currents of various frequencies. Examples of such apparatuses are the respirator itself, power supply units of the respirator or of other apparatuses, anesthesia apparatuses, gas monitors, blood pressure-measuring devices, and oxygen saturation-measuring devices ($S_pO_2$). However, block 107 may also receive other sensor signals, for example, signals from strain sensors (e.g., for the abdomen/thorax), acceleration sensors, sensors for measuring the thoracic impedance, etc. These exemplary devices and apparatuses are shown as sources of unwanted signals in FIG. 1C. However, additional signals originating from these devices and apparatuses may also be used, each in itself or combined with one another or combined with the ECG signal, to recognize certain patient-related situations (e.g., oxygen deficiency, drop in blood pressure, coughing, hiccups, sighing, apnea and/or fluctuations in the respiration rate) and to correspondingly adapt or to modify the control of, for example, the respirator. Examples of additional signals used are flow (respiratory flow), pressure (respiratory pressure), PEEP (Positive End Expiratory Pressure), blood pressure, as well as $CO_2$, $O_2$ and $S_pO_2$ concentration, NIV (Non-Invasive Ventilation), BP (blood pressure), anesthetic gas concentration, supply voltage and power frequency. However, the power frequency or the respiration rate itself can also be advantageously used, for example, for the adaptation and design of the filter frequencies or during the use of correlation/wavelet filtering in the slow path in order to extract the useful signal from the noise-containing signal in the fast path. It is obvious that the artifact analysis block 107 may also be used in the other exemplary embodiments according to FIGS. 1B, 2, 3A, 3B and 4.

Figure 1D:
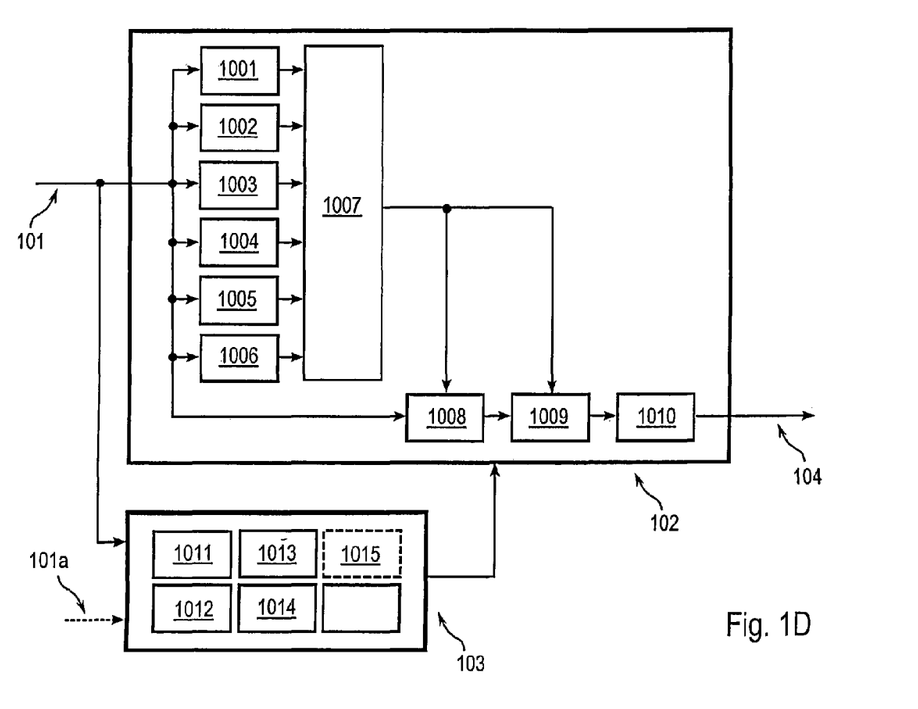
FIG. 1D is details of the "fast path" and of the "slow path" from FIGS. 1A through 1C.

FIG. 1D shows details of the fast signal path 102 and of the slow signal path 103 from FIGS. 1A and 1C, wherein the components shown may, however, also be contained in the respective paths from FIG. 1B. As can be seen in FIG. 1D, a noise-affected EMG or sEMG signal 101 (EMG=electromyogram/sEMG=Surface EMG) is present at the inputs of both the fast path 102 and of the slow path 103. This noise-affected EMG signal is fed in the fast path 102, for example, to a QRS detector 1001, a P wave detector 1002, a line artifact detector 1003, a crosstalk detector 1004, a hiccup detector 1005 or one or more other detectors 1006, which are disclosed in this specification, and at the same time to a baseline filter 1008. The outputs of these detectors are fed to a logic function block and/or fuzzy controller 10067, whose output is fed to the baseline filter 1008 and an artifact removal block 1009, wherein the output of the baseline filter is fed, in addition, to the artifact removal block. The output of the artifact removal block is then fed to the envelope curve calculation unit 1010, which outputs the noised-suppressed EMG or sEMG 104.

It is, furthermore, shown in FIG. 1D that the noise-affected EMG or sEMG signal 101 is also fed to the slow signal path 103, which contains the components explained above and whose output is coupled with the fast signal path 102. Furthermore, it is shown that different pneumatic signals 101a may be optionally fed to the slow signal path.

As is shown in FIG. 1D, the "fast path" block 102 contains, for different possible artifacts, a corresponding detector and a logic block, in which the appearance in time of the artifacts is logically linked. The linking may be performed, for example, by a logic combination of binary signals, which describe the detected or/and expected occurrence of specific artifacts. As an alternative, gradual changes over time may be used, which describe the probability of occurrence of specific artifacts. For example, the fuzzy logic shown is suitable for the combination of such changes.

As was already mentioned above, the "fast path" block contains (similarly to FIG. 6), furthermore, a baseline filter, a block for artifact removal as well as a block that performs the envelope curve calculation. The "baseline filter" and "artifact removal" blocks are modulated by the output signal of the logic block. For example, parameters of the baseline filter (e.g., of the ranking filter) are adapted depending on the degree to which an artifact is expected. Similarly, the "artifact removal" block becomes active only when it is driven correspondingly by the logic block.

All blocks of the fast path gain access to the parameters that the slow path 103 has determined, as was already mentioned. Thus, the detectors may be optionally adapted to the respective artifact properties. These parameters are, for example, ECG parameter 1011, crosstalk parameter 1012, hiccup parameter 1073, line artifact parameter 1014, parameter for spontaneous breathing and further parameters.

As will be described below with reference to FIG. 6, quality indicators, which can be used to improve the parameter determination in the slow path, can be calculated after the artifact removal. If, for example, it is found after removal of the artifacts that the artifacts were not removed completely, the corresponding artifact parameters could be adapted in order to achieve improved removal in the next step. The calculation of the quality indicators does not have to take place in the same path. However, if it is carried out in the slow path, signals from the fast path are needed for this. This corresponds to the return 317 in FIG. 3B, which will be described in more detail below.

FIG. 2 shows a second exemplary embodiment of the filter apparatus according to the present invention. In general, a cross linking of information between a plurality of signal paths takes place in this filter apparatus 200. The filter apparatus has a plurality of signal inputs 1 through n, which are designated by reference numbers 201-1 to 201-n, in order to receive a plurality of different physiological input signals (e.g., electromyographic signals, ECG signals, respiration rate, etc.) from a patient, which contain both a useful component and a noise component. Each of these input signals is fed both to a slow signal path 203-1 through 203-n and a fast signal path 202-1 through 202-n. The fast signal paths contain a preferably nonlinear filter each in order to bring about fast filtering, and the slow signal paths contain a preferably linear filter each in order to bring about slow filtering. The essentially noise-suppressed signals 204-1 through 204-n are present at the outputs of the respective fast signal paths. The outputs of the slow signal paths 203-1 through 203-n are connected each with an accounting/decision unit 205, whose outputs are coupled each with fast signal paths 202-1 through 202-n. The outputs of the slow signal paths can be coupled in this manner with desired fast signal paths in any desired manner. Results of the slow filtering of a signal can thus be applied to the fast filtering of another signal.

Figure 3A:
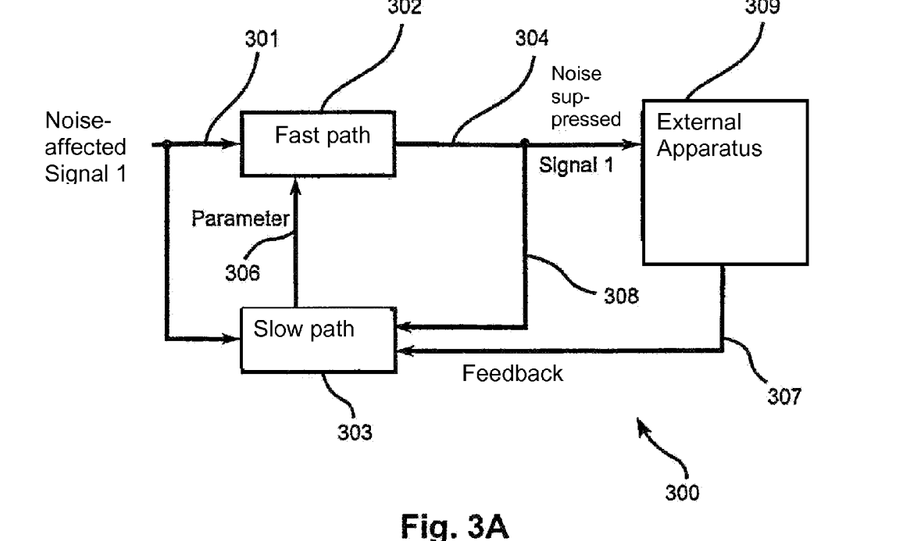
FIG. 3A is a schematic view of a third exemplary embodiment of the present invention, in which additional feedback is provided compared to the first exemplary embodiment from the output of the fast signal path or from the output signal of an external device to the slow signal path.
Figure 3B:
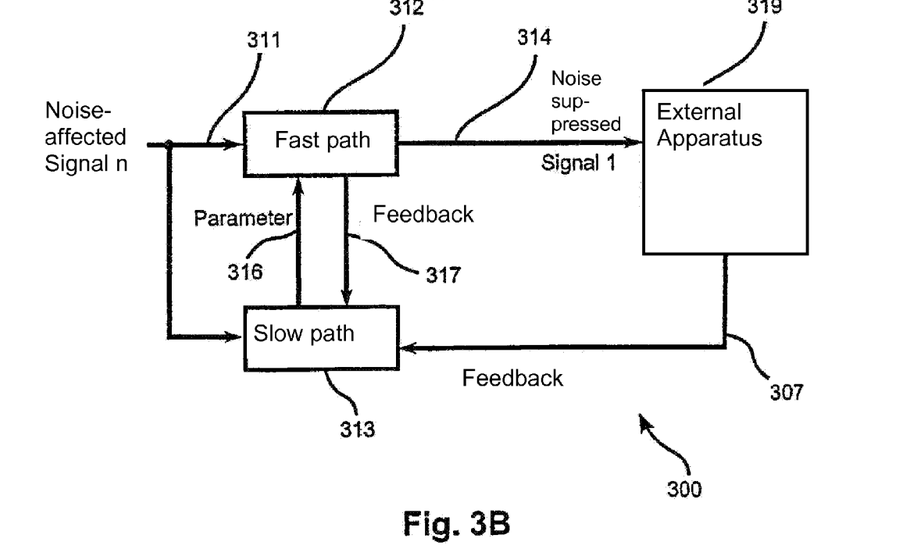
FIG. 3B is a variant of the exemplary embodiment from FIG. 3A.

FIGS. 3A and 3B show a third exemplary embodiment of the present invention. The basic designs of the filter apparatuses 300 and 310 from FIGS. 3A and 3B are similar to those of the filter apparatuses 100 and 110 from FIGS. 1A and 1B. Both filter apparatuses receive at their respective inputs 301 and 311 a noise-affected (physiological) signal, which is fed to a fast signal path 302/312 and to a slow signal path 303/313 connected in parallel thereto. The output 304/314 of the fast signal path has a nearly noise-suppressed signal applied to it, which is fed to an apparatus 309/319 (e.g., a respirator). As can be seen in FIG. 3A, the output signal 304 is returned as a feedback signal to the slow signal path 303. FIG. 3B shows an alternative embodiment, in which a signal is returned from any desired site of the nonlinear filter of the fast signal path 312 to any desired site of the linear filter of the slow signal path 313. Compared to the first exemplary embodiment, an additional feedback from an output of the fed external apparatus 309/319 to the slow signal path 303/313 is provided in the embodiments according to FIGS. 3A/3B. An automatic adaptation of signal processing is made possible hereby.

Figure 4:
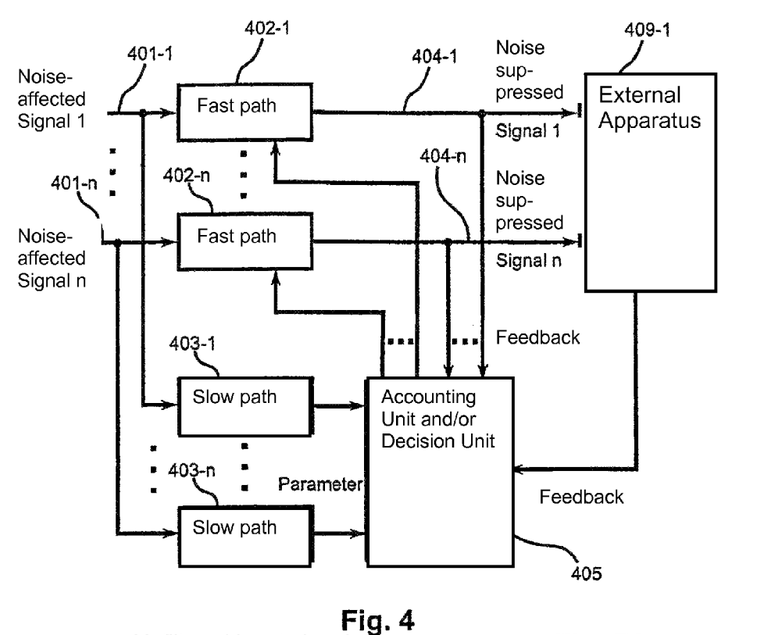
FIG. 4 is a schematic view of a fourth exemplary embodiment of the present invention, in which additional feedback is provided compared to the second exemplary embodiment from the outputs of the fast paths or from the output signal of the fed external device to the accounting/decision unit.

The exemplary embodiment shown in FIG. 4 is similar to the exemplary embodiment shown in FIG. 2, with the exception that an external apparatus 409-1 is coupled with the outputs 404-1 through 404-n of the fast signal paths 402-1 through 402-n. An output of this apparatus 409-1 is coupled with an input of the accounting/decision unit 405. Furthermore, the outputs of the fast signal paths 402-1 through 402-n are fed back to the accounting/decision unit 405.

Figure 5A:
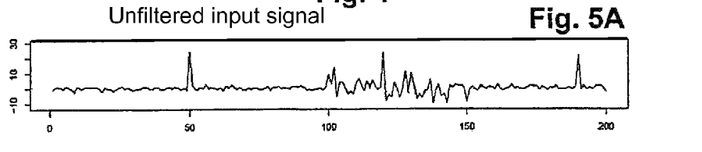
FIG. 5A is an exemplary view of an electromyographic signal interfered with by the ECG to explain the function of the first exemplary embodiment from FIGS. 1A through 1C.
Figure 5B:
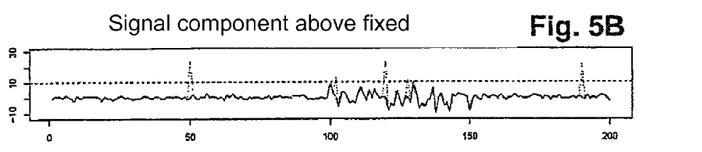
FIG. 5B is another exemplary view of an electromyographic signal interfered with by the ECG to explain the function of the first exemplary embodiment from FIGS. 1A through 1C.
Figure 5C:
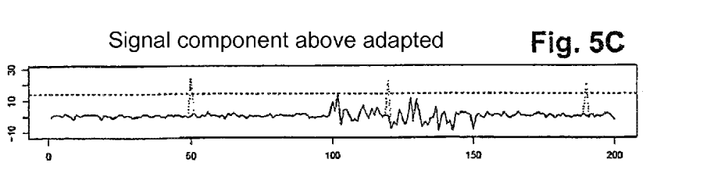
FIG. 5C is another exemplary view of an electromyographic signal interfered with by the ECG to explain the function of the first exemplary embodiment from FIGS. 1A through 1C.

FIGS. 5A through 5C show, as an example, views of an electromyographic signal interfered with by the ECG for explaining the function of the first exemplary embodiment. A nonlinear filter based on a outlier analysis (comparison with a fixed threshold, horizontal line drawn in a broken line) is embodied in the fast signal path in order to remove the R waves of the ECG (FIG. 5A, t=50, t=120, t=290). The result of the filtering is shown in FIG. 5B: The signal components indicated by dots were removed. However, a part of the useful signal, which is likewise removed (t=105, t=130), is also affected besides the R waves.

To make it possible to make a better distinction between useful signal and R waves, the slow path is provided now for FIG. 5C, instead of a fixed threshold, with a standard QRS recognition method (e.g., Pan-Tompkins [see J. Pan and W. J. Tompkins: A real time QRS detection algorithm, IEEE Transactions on Biomedical Engineering, Vol. BME-32, No. 3, March 1985]), which yields the level of the last R wave as the parameter for the fast path. This is used in the fast path for the distinction between useful signal and R wave by the threshold (broken line) being adjusted.

Figure 6:
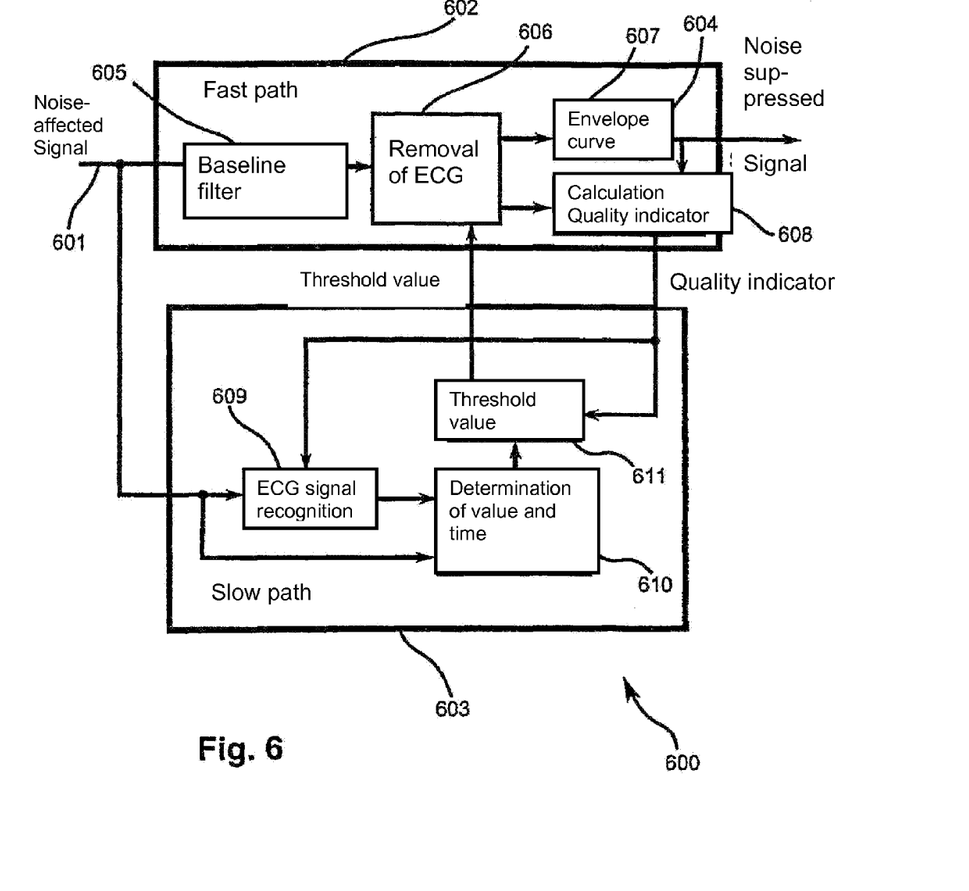
FIG. 6 is a view in which a detailed embodiment of the fast and slow signal path of the exemplary embodiment from FIG. 1B is shown.

FIG. 6 is a detailed view of a preferred exemplary embodiment of a filter apparatus 600 with a slow signal path and a fast signal path. The fast signal path 602 contains a baseline filter 605, a block 606 for removing an ECG signal (or outlier), an envelope curve calculation unit 607 and a unit 608 for calculating a quality indicator. The noise-affected input signal 601 is fed to an input of the baseline filter 605, whose output is coupled with a first input of block 606 for removing the ECG signal. The input signal now passes through the baseline filter, which removes low-frequency components (e.g., the R wave of the ECG signal contained in the input signal) of the input signal and may be designed as a linear filter with high-pass characteristic or as a nonlinear filter. Block 606 for the ECG removal has two outputs, of which a first output is coupled with an input of unit 608 for calculating a quality indicator. The output of the envelope curve calculating unit 607 yields the essentially noise-suppressed output signal 604, which is available at both the output of the fast signal path 602 (and hence at the output of the filter apparatus) and is fed to a second input of unit 608. Block 606 for removing an ECG signal has a second input, to which a dynamic threshold value, which is delivered by a unit 611 for the threshold value calculation of the slow signal path 603, is fed, which will be explained in more detail below. Furthermore, unit 608 has, for calculating a quality indicator, an output, at which a signal is outputted to a first input of unit 611 for the threshold value calculation and to a second input of an ECG signal recognition unit 609 of the slow signal path 603, this signal corresponding to the quality indicator, on the basis of which the threshold value calculation and the ECG signal recognition are performed.

The baseline filter 605 of the fast signal path 602 has, in general, the task of eliminating a baseline of the noise-affected input signal 601. The baseline typically consists of a constant component (frequency equaling zero) and low-frequency components. This baseline filter 605 is designed as a nonlinear filter here in order to obtain the shortest possible signal delay times, on the one hand, and, on the other hand, to change the shape of the ECG signal (or outlier) as little as possible. This is a problem especially because the R wave of the ECG usually has a triangular shape, which contains a constant component. This constant component is changed by the prior-art linear filters (here high-pass filters) towards a bipolar signal, because the R wave is subjected by the linear filtering to convoluting with the pulse response of the high-pass filter. The nonlinear filter used in the preferred exemplary embodiment is based on the use of a ranking filter. Signal filtering procedures based on ranking filters are, unlike sliding filtering or filtering based on predefined numbers of measured values in the manner of an arithmetic mean value formation, insensitive to outlier values in the signal. Ranking filters in the sense of the present invention are, for example, median filters, extreme value filters or so-called "smoothing" filters or "filters selecting a measured value," which allow a certain value to pass through the filter from a predetermined number of measured values fed into the filter according to a ranking, i.e., for example, the highest measured value, the second-highest measured value, the lowest measured value, the second-lowest measured value, a mean value from the number of measured values or a next higher or next lower value to the mean value from the number of measured values. Such filters are also known as the following filter types: "1-out-of-3 filters," "1-out-of-5 filters," "1-out-of-n filters," "minimum valve-from-5 filters," "maximum value-from-5 filters," "minimum-from-n filters," "maximum-from-n filters," "mean value-from-n filters" (often also called "median filters") and are frequently used, for example, in the area of image processing. The filter types described are mentioned within the framework of the present invention as an exemplary list only, which is in no way limited to the designation of a ranking filter but rather also comprises modifications and combinations of these types in the sense of the present invention. It is characteristic of such ranking filters that a measured value can pass unchanged through the filter, unlike in the case of other filters, in which a plurality of measured values lead to a new value at the filter output, for example, in case of an arithmetic mean value filtering. Differentiation with the unfiltered signal leads to the formation of a signal that still contains these outliers, but nevertheless removes the baseline. Outliers in the form of the R wave of the ECG signal are preserved in terms of their shape, but with a reduced height and length. This reduction of the height and length is linked with the delay time of the baseline filter 605.

Block 606 for removal of the ECG shall remove the signal components that can be attributed to the ECG. Due to the fact that, in particular, the shape of the R wave is not distorted by the baseline filtering by the baseline filter 605, the R wave of the ECG can be recognized in a simple manner by means of a threshold value detection. A suitable threshold value, which is delivered by unit 611 for the threshold value calculation by the slow signal path 603, is, however, necessary for an effective recognition with a low bit error rate at the same time. If an R wave (or an outlier) is recognized, the signal can be set at this site, e.g., to zero or to another suitable value. This is carried out according to the present invention in such a way that the subsequent envelope curve calculation is not comprised substantially. On the one hand, the time period of the outlier or the time period during which the signal is set at a suitable value should be as short as possible to prevent any useful signal components from being replaced. In the present filter apparatus, the nonlinear filters mentioned have the advantage over linear filters that there is no post-pulse oscillation (ringing), which causes outliers not to be prolonged in time by the baseline filter 605. On the other hand, the calculation of the envelope curve must take place during the time of the removed outlier such that the envelope curve signal changes continuously, rather than discretely. The envelope curve is preferably extrapolated during the time of the removed outlier in order to obtain the smoothest possible envelope curve shape.

Calculation of the envelope curve is meaningful for an application for controlling a respirator in order to generate a triggering time from it. The information on, e.g., the sites at which outliers were recognized can be used in the envelope curve calculation unit 607, e.g., to guarantee a smooth envelope curve shape.

A quality indicator, which characterizes the quality of the stage in question, can be calculated from the signals of the ECG removal and/or envelope curve calculation as well as from the internal variables of the ECG removal. This quality indicator parameter can be used in the slow signal path 603. The quality indicator can indicate, for example, the probability with which the outlier was recognized correctly, i.e., how certain the decision to eliminate the outlier was. As an alternative, the quality indicator may represent a signal-to-noise ratio.

As is shown in FIG. 6, the slow signal path 603 contains an ECG signal recognition unit 609 (or—stated in general terms—a unit for recognizing outliers), a unit 610 for determining the value and the time of the ECG and of the outlier, as well as a unit 611 for threshold value calculation. The ECG signal recognition unit 609 has a first input, at which the noise-affected input signal 601 is present, and a second input, to which the parameter signal of the quality indicator is fed from unit 608 for calculating the quality parameter. The ECG signal recognition unit 609 has, furthermore, an output, which is coupled with a first input of unit 610. Unit 610 has a second input, at which the noise-affected input signal 601 is likewise present, and an output, which is coupled with the second input of unit 611.

The ECG signal recognition unit 609 typically uses a standard method, e.g., a Pan-Tompkins algorithm. The signal delay time associated herewith is of secondary significance. In particular, relatively slow linear filters can be used for filtering. Unit 609 usually yields the time, e.g., for the maximum of the ECG, which can be normally attributed to the R peak. However, this time cannot be determined with sufficient accuracy because of the internal signal processing in the ECG signal recognition unit. To obtain the exact time of the maximum and the corresponding value, a comparison is made with the original signal in unit 610 for determining the value and the time of the ECG. This information is then used in the threshold value calculation to determine a suitable threshold value for the removal of the ECG in the fast signal path 602.

The quality indicator, which was calculated in the fast signal path 602, can then be used to improve the ECG signal recognition and the threshold value calculation.

Embodiments that are directed towards the removal of ECG artifacts were described above. In addition or as an alternative, the filter apparatus according to the present invention may be designed to filter line noises of 50 Hz or 60 Hz in an a.c. network with 230 V or 110 V out of the input signal. The signal processing takes place in more than one path here as well, i.e., in at least one fast signal path (corresponding to the requirement that the delay should be as short as possible) and in at least one slow path, and the results of the calculations of the slow part must be available only later (e.g., after the end of the current breath).

It can be determined, in summary, that the following signal parameters, which are used in the fast signal path for the signal processing, are preferably determined in the at least one slow signal path:

ECG parameters, for quantifying the degree to which the physiological signal is affected by cardiac artifacts, e.g., for the decision on whether QRS recognition and QRS removal are to be performed at all;

further specific ECG parameters, e.g., parameters of the R waves, of the P waves and of the QRS complexes, wherein:

individual and mean amplitude level width or power of the artifacts as well as the spread (possibly additionally other parameters of the signal amplitude distribution);

individual and mean distance between the artifacts as well as the spread (possibly additionally other parameters of the signal amplitude distribution), individual and mean amplitude level or power of the signal sections between the artifacts as well as the spread thereof (possibly additionally other parameters of the signal amplitude distribution);

expectation window (yes/no) for the expected occurrence of specific artifacts and of the useful signal;

swallowing parameters, e.g., frequency of occurrence and intensity of the artifact; crosstalk parameters for quantifying the degree of interference with the; physiological signal due to crosstalk (electrical activity of other muscles) or motion. This can be performed by analyses of the correlation of the physiological signal with pneumatic signals (e.g., airway flow);

line artifact parameters for quantifying the degree of interference with the physiological signal due to line artifacts (50/60 Hz), e.g., for recognizing electrodes that have become loose or have even fallen off;

parameters for spontaneous breathing, e.g., respiration rate, duration of breath, duration of inspiration, duration of expiration, and here the individual value and the mean value as well as the spread (possibly other parameters of the distribution), e.g., for setting the parameters of the envelope curve calculation;

alternatively: Gradual changes over time, which describe the probability of occurrence of specific artifacts or of the useful signal.

It should be noted that the above parameters are shown in FIG. 1D in the "slow path" block.

These parameters are used to set at least one (constant or dynamically variable) threshold in the at least one fast signal path such that the artifacts can be easily distinguished from the rest of the useful signal, and to subsequently remove the artifacts from the useful signal.

The removal of the artifacts is performed, in principle, with a (possibly dynamic) lead and a (possibly dynamic) time lag. This means that the time window that contains the artifact is either constant or depends on the parameters of the artifacts (e.g., the width and/or height) determined in the slow signal path. For artifacts that are, e.g., so small that they cannot be accurately detected by means of a threshold (e.g., P waves), it is possible to cut out the artifact hardly by means of an expectation window determined from the slow path (or of a gradual probability curve) and to replace it by a simulated useful signal or to make it inactive in another manner by adaption of signal processing methods. The latter can be performed by switching the filter characteristic or by gradual adaptation of the filter parameters—within the expectation window or depending on the probability curve.

Finally, an indicator, which represents the degree of the electric activity of the muscle, is determined for the useful signal from which the artifacts have been removed. The envelope curve, a counter for counting the zero crossings of the signal, the curve of the RMS values or another power indicator can be used for this. The power indicator of the useful signal from which artifacts have been removed is used to monitor the breathing activity and/or to control respiration by the respirator.

The signal filtering described in FIG. 1B is shown once again at this point in a special embodiment according to the present invention of a method according to the present invention on the basis of programmed source codes for implementation in software.

In a method for the real-time filtering of physiological signals with a useful component and with a noise component, a noise-affected physiological signal 111 is fed as an input signal at a signal input of a fast signal path 112 and, in parallel and simultaneously in time hereto, into a signal input of a slow signal path 113, fast filtering is performed in the fast signal path 112,
slow filtering is performed in the slow signal path 113,
a parameter 116 of the slow signal path 113 is fed into the fast signal path 112,
a feedback signal 117 of the fast signal path 113 is returned into the slow signal path 112, and
a noise-suppressed physiological signal 114 is present as a filtered output signal,
which is not delayed compared to the passage through the fast signal path 112.

Fast nonlinear filtering is carried out in the fast signal path 112 in this method according to the present invention, and the noise component of the physiological signal is not completely suppressed by the fast filtering. The fast filtering in the fast signal path 112 is preferably performed in a nonlinear manner.

Slow filtering is performed in the slow signal path 113 in this method according to the present invention, and the noise component of the physiological signal is suppressed essentially completely by the slow filtering. The slow filtering in the slow signal path 113 is preferably performed in a linear manner.

The slow signal path 113 and the fast signal path 112 are passed through in parallel in this method according to the present invention, and a noise-suppressed signal 113, which contains essentially the useful component of the physiological signal and in which the noise component of the physiological signal is essentially suppressed, is obtained as a filtered output signal after the parallel passage.

While specific embodiments of the invention have been shown and described in detail to illustrate the application of the principles of the invention, it will be understood that the invention may be embodied otherwise without departing from such principles.

The invention claimed is:

1. A filter apparatus comprising:
a signal input, at which an input signal is present, which input signal contains a useful component and a noise component;
a fast signal path, the fast signal path having a fast signal path input and a fast signal path output;
a slow signal path arranged in parallel to the fast signal path, the slow signal path having a slow signal path input and a slow signal path output;
a signal line coupling the slow signal path output with the fast signal path to change a characteristic of said fast signal path, wherein the signal input is coupled with the fast signal path input and of the slow signal path input, wherein the fast signal path contains a filter to bring about fast filtering of the input signal and wherein the slow signal path contains a filter to bring about slow filtering of the input signal;
a signal output coupled with the fast signal path output and at which an output signal, which contains essentially useful components of the input signal, is present; and
another signal line via which a signal is returned from the fast signal path to the slow signal path to affect the functional characteristic of the slow filter path, wherein an output of the fast signal path is coupled via the another signal line with an input of the slow signal path and wherein physiological signals from a patient, which are used after their filtering to drive a respirator, are present at the signal input, wherein said input signal is a physiological signal from a patient, said physiological signal passing through said fast signal path and through said slow signal path, wherein a signal travel time in said fast signal path is shorter by a factor of at least two than a signal travel time in said slow signal path, said another signal line connecting said fast signal path output of said fast signal path with said slow signal path input of said slow signal path to change said functional characteristic of said slow filter path, wherein said filter of said fast signal path comprises nonlinear properties, said filter of said slow signal path comprising linear properties or an adaptive filter.

2. A filter apparatus in accordance with claim 1, wherein the slow signal path is provided with an artifact analysis block, which has inputs for additional signals.

3. A filter apparatus comprising:
a plurality of signal inputs, each having an input signal, which contains a useful component and a noise component;
a plurality of fast signal paths arranged in parallel;
a plurality of slow signal paths arranged in parallel;

wherein each of the plurality of signal inputs is coupled with an input of the plurality of fast signal paths arranged in parallel and of the plurality of slow signal paths arranged in parallel, wherein each fast signal path contains a filter to bring about fast filtering of the input signal, wherein each slow signal path contains a filter to bring about slow filtering of the input signal;

an accounting/decision unit;

signal lines, wherein each slow signal path is coupled with corresponding inputs of the accounting/decision unit via the respective signal lines, wherein each fast signal path is coupled with corresponding outputs of the accounting/decision unit via the respective signal lines; and a plurality of signal outputs, which are coupled each with outputs of the fast signal paths and at which respective output signals, which contain essentially useful components of the input signals, are present, wherein a signal travel time in each of said fast signal paths is shorter by a factor of at least two than a signal travel time in each of said slow signal paths, wherein physiological signals, which are present at said signal inputs and which are present at said signal outputs after their filtering by the filter apparatus, are used to drive a respirator, said filter of each of said plurality of fast signal paths comprising nonlinear properties and said filter of each of said plurality of slow signal paths comprising linear properties or an adaptive filter, said outputs of said fast signal paths being coupled with corresponding inputs of said accounting/decision unit via respective signal lines.

4. A filter apparatus in accordance with claim 3, wherein the outputs of the fast signal paths are coupled with corresponding inputs of the accounting/decision unit via the respective signal lines.

5. A filter apparatus in accordance with claim 3 for the real-time filtering of physiological signals from a patient, which are used after their filtering to drive a respirator.

6. A filter apparatus in accordance with claim 3, wherein the slow signal path is provided with an artifact analysis block, which has inputs for additional signals.

7. A method for the real-time filtering of physiological signals with a useful component and with a noise component, the method comprising the steps of:

providing a fast signal path, through which the physiological signal is to pass, with a signal input and with a signal output;

providing a slow signal path through which the physiological signal is to pass in parallel thereto with a signal input and with a signal output;

providing a connection and connecting the signal output of the fast signal path with the signal output of the slow signal path as a signal output;

providing another connection and connecting the signal output of the fast signal path with the signal input of the slow signal path;

coupling the physiological signal in parallel into the input of the fast signal path and into the input of the slow signal path;

passing the physiological signal through the fast signal path fast, providing a filtered output signal, which contains essentially the useful component of the physiological signal and in which the noise component of the physiological signal is not suppressed completely by the fast filtering at the signal output of the fast signal path, wherein the characteristic of the fast signal path is affected via the connection; and passing the physiological signal through the slow signal path slowly, wherein the characteristic of the slow signal path is affected via the further connection, and providing a filtered output signal, which contains essentially the useful component of the physiological signal and in which the noise component of the physiological signal is essentially suppressed by the slow filtering at the signal output of the slow signal path, wherein a filtered output signal, which contains essentially the useful component of the physiological signal and in which the noise component of the physiological signal is essentially suppressed, is present at the signal output without time delay relative to the signal output of the fast signal path, wherein a signal travel time in said fast signal path is shorter by a factor of at least two than a signal travel time in said slow signal path, wherein a parameter of the slow signal path is provided into the fast signal path via a signal line, wherein a feedback signal is provided from said fast signal path to said slow signal path via another signal line to affect a functional characteristic of said slow filter path.

8. A method for the real-time filtering of physiological signals with a useful component and with a noise component, the method comprising the steps of:

feeding a noise-affected physiological signal as an input signal at a signal input of a fast signal path and, in parallel and simultaneously in time therewith, into a signal input of a slow signal path;

slow filtering the noise-affected physiological signal in the slow signal path;

feeding a parameter of the slow signal path into the fast signal path;

fast filtering said noise-affected physiological signal via said fast filter path based on said parameter to provide a noise-suppressed physiological signal, which is not delayed relative to the pass through the slow signal path of the physiological signal, as a filtered output signal; and returning a feedback signal of the fast signal path into the slow signal path, wherein a threshold is determined based on said parameter, said noise-affected physiological signal being filtered via said fast filter path based on said threshold, wherein a signal travel time in said fast signal path is shorter by a factor of at least two than a signal travel time in said slow signal path, wherein said fast signal path has a filter with nonlinear properties and said slow signal path has a filter with linear properties or an adaptive filter.

9. A method in accordance with claim 7, wherein the noise component of the physiological signal is not suppressed completely in the fast signal path.

10. A method in accordance with claim 7, wherein the noise component of the physiological signal is suppressed essentially completely in the slow signal path.

* * * * *